(12) United States Patent
Xu

(10) Patent No.: US 6,197,509 B1
(45) Date of Patent: Mar. 6, 2001

(54) METHOD OF ANALYZING DNA USING CONTIGUOUS REPEATS

(75) Inventor: Weiming Xu, Cambridge (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/155,942

(22) PCT Filed: Apr. 4, 1997

(86) PCT No.: PCT/GB97/00949

§ 371 Date: May 13, 1999

§ 102(e) Date: May 13, 1999

(87) PCT Pub. No.: WO97/38130

PCT Pub. Date: Oct. 16, 1997

(30) Foreign Application Priority Data

Apr. 10, 1996 (GB) .................................................. 9607440

(51) Int. Cl.[7] .............................. C12Q 1/68; C12P 19/34; C07H 21/04
(52) U.S. Cl. ............................ 435/6; 435/91.2; 536/23.2; 536/23.5; 536/24.31; 536/24.33
(58) Field of Search ................... 435/6, 91.2; 536/24.31, 536/24.33, 23.2, 23.5

(56) References Cited

U.S. PATENT DOCUMENTS 5,882,908 * 3/1999 Billiar et al. .................... 435/189

OTHER PUBLICATIONS

Spitsin, S.V. et al. Molecular Medicine 2(2):226–235, Mar. 1996.*

Spitsin, S.V. et al. GenBank Accession No. Z49251, Jan. 1997.*

* cited by examiner

Primary Examiner—Carla J. Myers
Assistant Examiner—Diana Johannsen
(74) Attorney, Agent, or Firm—Pillsbury Madison & Sutro

(57) ABSTRACT

A novel, highly polymorphic DNA marker based on the pentanucleotide repeat $(CCTTT/GGAAA)_n$ has been identified in the human inducible nitric oxide synthase (iNOS) gene. Twelve different alleles, having between 7 and 18 repeats, have been identified. The repeat is highly polymorphic in the human population and so lends itself to use as a microsatellite marker with uses in, for example, forensic medicine, population studies, family linkage studies and disease diagnosis.

17 Claims, 10 Drawing Sheets

Restriction map of 5'end upstream region of human inducible nitric oxide synthase gene and (CCTTT/GGAAA)n repeat region in 383bp of PstI fragment

```
CTGCAGCAAG CCATAAACAT TCCCNTGGAG AAAGATGCTT TCCCAGCATC AAGATGAGAA    60
GACGTCGTTC GGTATTTGTA AGGGNACCTC TTTCTACGAA AGGGTCGTAG TTCTACTCTT

GATAACTTTT ATCAGCTCAG AGATGGCACC AGAGCCATCT ACAAATACCA AACAAACCTT   120
CTATTGAAAA TAGTCGAGTC TCTACCGTGG TCTCGGTAGA TGTTTATGGT TTGTTTGGAA

GCTATCCTAC TCCTTAGCTC ACTTCCACAT GTTTACCTTC TCACAGCTTG CCACCCCTGG   180
CGATAGGATG AGGAATCGAG TGAAGGTGTA CAAATGGAAG AGTGTCGAAC GGTGGGGACC

AAGCCTACAA CTGCATTCGT CTTGTCACCT CTTTCTTCTT TCCTTTCCT TCTCTTTCCT    240
TTCGGATGTT GACGTAAGCA GAACAGTGGA GAAAGAAGAA AGGAAAGGA AGAGAAAGGA

TTCCTTTCTT TTCCTTTCCT TTCCTTTCCT TTCCTTTCCT TTCCTTTCCT TTCCTTTCCT   300
AAGGAAAGAA AAGGAAAGGA AAGGAAAGGA AAGGAAAGGA AAGGAAAGGA AAGGAAAGGA

TTCCTTTCCT CCTTTCCCTC TTTTTTTTCC TTTTTTTTTT GAGACAGGCT AGGGTGCAGT   360
AAGGAAAGGA GGAAAGGGAG AAAAAAAAGG AAAAAAAAAA CTCTGTCCGA TCCCACGTCA

GGCGCGACCA TAGCTCTCTG CAG    383
CCGCGCTGGT ATCGAGAGAC GTC
```

METHOD OF ANALYZING DNA USING CONTIGUOUS REPEATS

FIELD OF THE INVENTION

This invention concerns analysis of DNA particularly for examining genetic markers, which is useful in, for example, forensic medicine, population studies, family linkage studies and disease diagnosis.

BACKGROUND TO THE INVENTION

It is known that there are simple nucleotide sequences in the human genome that can occur in different numbers of repeats in different individuals, giving rise to a range of different alleles or variants of different length that can be used as genetic markers to typify the DNA of an individual.

Tandem repeat minisatellite and microsatellite regions in vertebrate DNA frequently show high levels of allelic variability in the number of repeat units. These highly informative genetic markers have found widespread applications in population genetics, forensic science, medicine and other natural scientific studies. For example, these markers can be used for linkage analysis, determination of kinship in paternity and immigration disputes and for individual identification in forensic medicine. In a minisatellite system, a core DNA sequence unit is usually 15 or more base pairs. To date most studies and applications of such systems have relied on Southern blot estimation of allele length, which requires at least 50 ng of relatively undegraded DNA. It is often very difficult to extract such large amounts of DNA from many forensic samples such as blood and semen stains.

Microsatellites, on the other hand, are short tandemly repeated (STR) polymorphic DNA sequences which are most commonly in the form of dinucleotide repeats such as (dC-dA)n, but can also be trinucleotide and tetranucleotide repeats. For a further discussion, see Pena. S. D. J. and Chakraborry, R. (1994). Paternity testing in DNA era. Trends in Genetics Vol.10, 204–209. Microsatellites can be amplified using the polymerase chain reaction (PCR) and the resulting ampileons normally range from 80–800 base pairs (bps) in length and so are well suited to processing in automated sequencing machines which are now widely used for gene scanning and typing. (See Read, P. W. et al (1994), Chromosome-specific microsatellite sets for fluorescence based, semiautomatic genome mapping. Nature Genet. 7,390–395.) To date, most microsatellite polymorphisms have been based upon dinucleotide repeats. Because of the very small size difference between adjacent alleles, some of the results can be difficult to interpret. Tri and tetranucleotide repeats are easier to use but occur less frequently in the human genome. Expansion of trinucleotide repeat sequences has also been implicated in a number of genetic diseases, including Huntingdon's disease, fragile X syndrome and myotoaic dystrophy.

The present invention is based on the discovery in the human inducible nitric oxide synthase (iNOS) gene of a pentanucleotide repeat (CCTTT/GGAAA)n. The repeat is located approximately 2.8 kb 5' end of upstream promotor region of the iNOS gene on 17q11.1-q11.2. Investigations have shown this pentanucleotide repeat (which is referred to for convenience as Xu-1) occurs in widely varying numbers in different individuals; so far, 12 different variants or alleles have been detected, having between 7 and 18 contiguous Xu-1 repeats. The different alleles are referred to as A7, A8 ... A18. Because the Xu-1 repeat is highly polymorphic in the human population, the repeat leads itself to use as a microsatellite marker with uses in, for example, forensic medicine, population studies, family linkage studies and disease diagnosis.

SUMMARY OF THE INVENTION

In one aspect the present invention provides an a method of analysing a sample of DNA to determine the number of contiguous repeats of the sequence (CCTTT/GGAAA) in the iNOS gene.

The number of repeats is typically in the range 7 to 18.

By analysing DNA in this way, a determination can be made of the number of Xu-1 repeats in a particular DNA sample, that is which allele or alleles (usually one or more of A7 to A18) are present The sample may be, for example, a sample of blood, semen, saliva, buccal cells or any other suitable biological material.

Because the Xu-1 repeat is a pentanucleotide repeat, it is easier to distinguish adjacent alleles simply on the basis of size than is the case for smaller repeating units. Experiments have also shown that there is considerable variation in the two alleles (one from each chromosome) of different individuals. The heterozygosity has been calculated as 0.841. The Xu-1 repeat is therefore highly polymorphic and hence has significant valve as a genetic marker (the Xu-1 marker) that is easy to use.

Samples are conveniently analysed by use of the polymerase chain reaction (PCR), enabling the method of the invention to be performed on small quantities of sample. A pair of PCR primers has been designed for this purpose, generating products in the range about 170 to 225 base pairs (bp) in size. The forward primer is 5'-ACCCCTGGAAGCCTACAACTGCAT-3' (Seq. ID No. 1). The reverse primer is 5'-GCCACTGCACCCTAGCCTGTCTCA-3' (Seq. ID No. 2).

The resulting products may be sequenced to determine the number of Xu-1 repeats. Alternatively, fragment length can simply be determined, eg by running on an electropheretic gel, enabling calculation of the number of Xu-1 repeats.

Heterozygosity can be increased substantially by using the Xu-1 marker in conjunction with another genetic marker. For example, good results have been obtained using the Xu-1 marker with a known microsatellite marker based on the polymorphic trinucleotide repeat (ATT/TAA) present in the neuronal nitric oxide synthase (NOS1) gene in repeat numbers ranging from 5 to 13. PCR primers have been designed for use with the NOS1 marker to generate products in the range 110 to 138 bp (ie distinct in size from the Xu-1 marker products), that can be used under the same PCR conditions as the Xu-1 primers. The forward primer is 5'-GAAATTGGTCATAGTGGGAATG-3' (Seq. ID No. 3). The reverse primer is 5'-GTGTTGGTGAACCAACCCTCCTAA-3' (Seq. ID No. 4).

PCR reactions for the 2 markers can thus be run together, and by using different labels (eg green and blue) for the primers, the PCR products can be detected simultaneously on the same gel. By using these 2 markers together, heterozygosity is incresed to about 99%.

Experiments have shown that there are significant differences in the distribution of alleles with different numbers of the Xu-1 repeat in different ethnic groups. The Xu-1 marker may therefore be of value in population studies, immigration disputes, paternity determination and forensic studies.

Furthermore, because the Xu-1 marker is located in the 5' end of human iNOS gene, which has been implicated in certain common human diseases, such as Alzheimer's disease, hypertension, diabetes and cancers, the marker can be used in allelic association studies and mutation analysis for the diseases. For example, a strong allelic association has already been detected between the repeat number and the senile dementia Lewy body (SDLT) variant of Alzheimer's disease, which represents about one quarter of all cases of Alzheimer's disease. Mutations in flanking sequences have also been detected in some cases of colon cancer. The iNOS gene is also involved in tissue transplantation. The polymorphic marker described in this invention also could be used in genotype typing for tissue transplantation.

The invention will be further described, by way of illustration, in the following Examples and by reference to the accompanying Figures.

BRIEF DESCRIPTION OF THE FIGURES

FIG. 1B shows the sequence of a 383 base pair Pst1 fragment (the upper strand of which is Seq. ID No. 5) included in FIG. 1, with Pst1 sites underlined and 11 contiguous Xu-1 repeats marked by boxes;

EXAMPLE 1

Figure 1A:
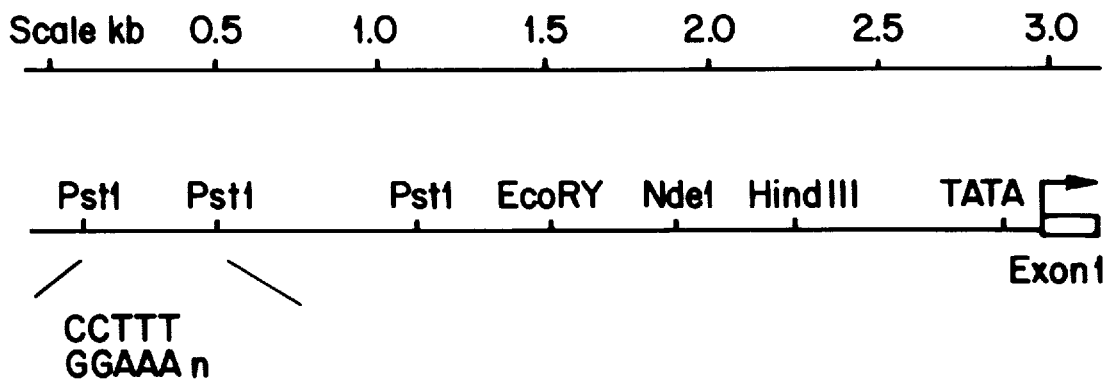
FIG. 1A is a restriction map of 5' end upstream region of the human inducible nitric oxide synthase (iNOS) gene, including the Xu-1 repeat region.

The new pentanucleotide repeat, (CCTTT/GGAAA)n on which the present invention is based was identified from a comid clone. pCOS4 (described by Xu, W., Charles, I., Moncada, S., Gorman P., Sheer, D., Liu, L., and Emson, P. C. (1994) in Mapping of the genes encoding human inducible and endothelial nitric oxide synthase (NOS2 and NOS3) to the pericentric region of chromosome 17 and to chromosome 7, respectively. Genomics 21, 419–422), which contained a 35 kb human genomic insert, which has also been shown to contain the human inducible mitric oxide synthase (iNOS) gene coding region and its promoter region. A restriction map of the 5' upstream end of the gene is shown in FIG. 1A. In order to clone human promoter region of the inducible nitric oxide synthase gene, the cosmid was shot-gun cloned with Pst1 and HindIII restriction enzymes into pBluescript SK vector. Subclones were then sequenced using an ABI automatic sequencer with M13 universal and reverse primers. One of the Pst1 subclones, clone number 512, has been shown by sequencing studies to contain eleven perfect contiguous pentanucleotide repeats. (CCTTT/GGAAA)11, that is a stretch of fifty-five bases pairs of human genome, located 2.8 kb of 5' end of the major transcription initiation site of the human inducible nitric oxide synthase gene. The sequence of this 383 base pair fragment (Seq. ID No. 5) is shown in FIG. 1B, with 11 pentanucleotide repeats marked in boxes. It will be seen that the repeats and flanking regions constitute polypurines in one strand and polypyrimidines is the other strand spanning over 130 base pairs, which is highly unusual in a microsatellite because of the instability of such sequences.

EXAMPLE 2

A pair of specific oligonucleotide primers were designed to use the polymerase chain reaction (PCR) directly to amplify the polymorphic pentanucleotide repeat from the genomic DNA from a range of human DNA samples.

The DNA can be isolated from either blood or buccal cells of the saliva or any other biological sources which containing nuclei. The DNA extraction can be done in all cases using standard SDS-Proteinase K-Phenol procedure. (Sambrook, J., Fritsch, E. F. & Maniatis, T. (1989). Molecular cloning. Laboratory manual Cold Spring Harbor Laboratory Press, New York.)

A pair of flanking PCR primers designed to amplify the genomic DNA from human blood genomic DNA were as follow: The forward primer is 5'-ACCCCTGGAAGCCTACAACTGCAT-3' (Seq. ID No. 1). The reverse primer is 5'-GCCACTGCACCCTAGCCTGTCTCA-3' (Seq. ID No. 2). The primers are double underlined in FIG. 1B. The forward primer is 5' end labelled with fluorescent dye 6-carboxyfluorescein (6-Fam) (Oswel DNA Services, University of Southampton, Southampton SO16 7PX) or Hex phosphotamidites (Applied Biosystems). Primers were synthesised, labelled and HPLC-purified using standard methods (Oswel DNA Services, Southampton).

The PCR protocol is as follows:

i) Reagent Mixture

The following reagents were mixed in a labelled 0.5 ml double-snap-cap microcentrifuge tube:

| Reagent | Amount |
| --- | --- |
| Template | 1 µl 50–200 nm Genomic DNA |
| 10 × PCR buffer II (Cetus, N808-0010, E8064) | 5 µl |
| dNTP Mix (2.5 mM each, Pharmacia, 27-2035-01) | 5 µl |
| 25 mM MgCl$_2$(Cetus, N808-0010, E 0843) | 3 µl |
| Forward primer (200 µg/ml, 6 Fam labelled) | 1 µl |
| Reverse primer (200 µg/ml) | 1 µl |
| dH$_2$O (distilled or deionized water) | 33.5 µl |
| AmpliTaq DNA polymerase (Cetus, N801-0060) | 0.5 µl (2.5 Units) |
| Final Reaction Volume | 50 µl |

(AmpliTaq is a Trade Mark of Roche Molecular Systems, Inc.) (dNTP=deoxynucleotide triphosphate. Taq DNA polymerase=DNA polymerase isolated from *Thermus aquaticus*.)

The reaction mixture was overlaid with one drop of mineral oil (Sigma No. M5904) (approximately by 40 µl).

ii) PCR Reaction

PCR is carried out using a Perkin Elmer Cetus Model 480 (or equivalent machine) as follows.

1. Place the tubes in a thermal cycler.
2. Immediately after placing the tubes in the thermal cycler, begin thermal cycling as follows:
   a) preheat to 96° C.
   b) 96° C. for 30 seconds
   c) 30 cycles as follows: 94° C. for 1 min., annealing at 50° C. for 1 min., and polymerising at 72° C. for 1 min.
   d) 72° C. for 10 min.
3. Rapid thermal ramp to 4° C. and hold.

The sizes of the PCR products range from about 170 bp to 225 bp. dependent on the number of pentanucleotide repeat units.

iii) Electrophoresis

The PCR products are then loaded directly on an Applied Biosystems Model 373A DNA Sequencer using 6%-urea polyacrylamide gel. Running conditions are at 2000V, 26 watts for 4 to 12 hours. The GENESCAN option is used to start running the gel. (Genescan is a Trade Mark of Applied Biosystems, Inc.)

Preparing and loading the samples was carried out as follows:

1. Prepare a mixture of the following reagents:
   5 µl detonized formamide
   0.5 µl Rox labelled DNA marker (GENESCAN-2500)
2. Add 4 µl of this mixture to each tube and agitate vigorously. Centrifuge the solution briefly.
3. When the gel is ready for loading, heat the samples at 90° C. for 2 minutes to denature, then transfer them immediately onto ice.
4. Load the samples onto an Applied Biosystems 373A DNA Sequence according to the instructions in the User's Manual.

iv) Genescan and Analysis

The GENESCAN 672 software is used to collect and analyse the data automatically. This software can be used not only to collect electroophoretic data across all 24 or 36 lanes, but also accurately to identify and analyse the different lanes of the fragments. The internal standard, Rox-GENESCAN 2500, permits accurate and precise base identification and accurate sizing of the fragments. If an automatic DNA sequencer is not available, other methods such as use of radioactive labels can be used instead to detect the PCR products.

v) Sequence Analysis

The PCR products can also be cloned into the Bluescripts pKS—vector using the T-vector cloning system (Stratagene, Cambridge, UK) and sequenced by TaqDyeDeoxy terminator cycle sequencing with an Applied Biosystems Model 373A DNA Sequencer, using vector universal and reverse primers. The products can also directly sequenced using the PCR DNA gel purification system from Qiegen, following the manufacturers instructions, with 3 pmol of Primer A or B.

EXAMPLE 3

Figure 2:
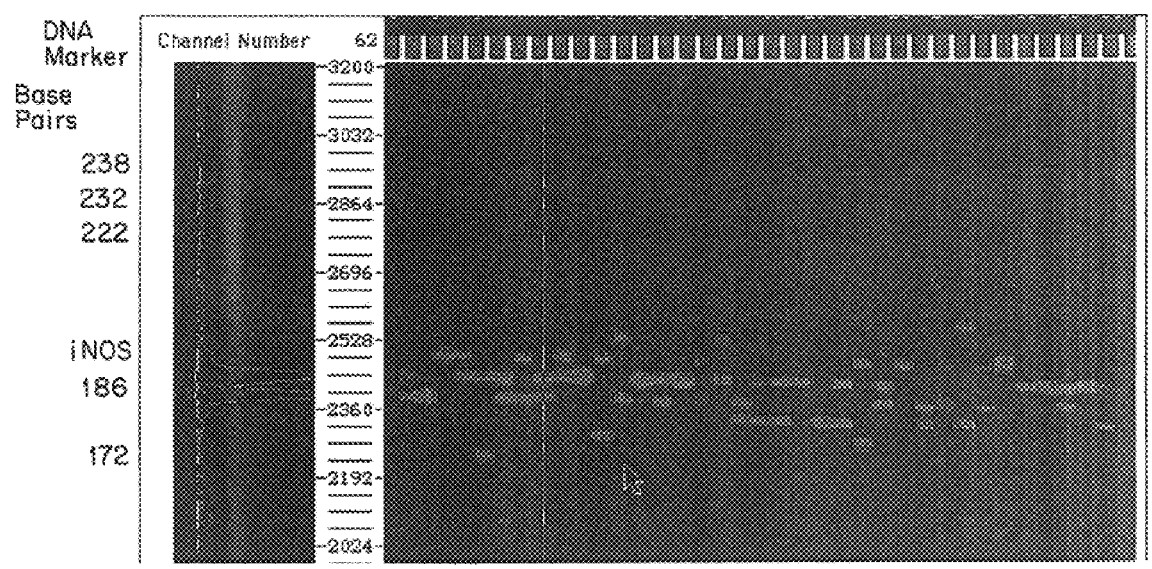
FIG. 2 shows an electrophoretic gel showing different Xu-1 alleles from different individuals.

Using the primers and techniques described in Example 2. DNA from 36 unrelated individuals was examined. The resulting electrophoretic gel is shown in FIG. 2. A series of (red) bands (not visible in the Figure) show internal DNA size markers (Genescan 2500, Rox), as indicated on the left of the Figure. The brighter (blue) bands across the middle of the gel are produced by 6-Fam fluorescently labelled primer A, and these show the presence of different repeat lengths, demonstrating polymorphism.

EXAMPLE 4

Figure 3:
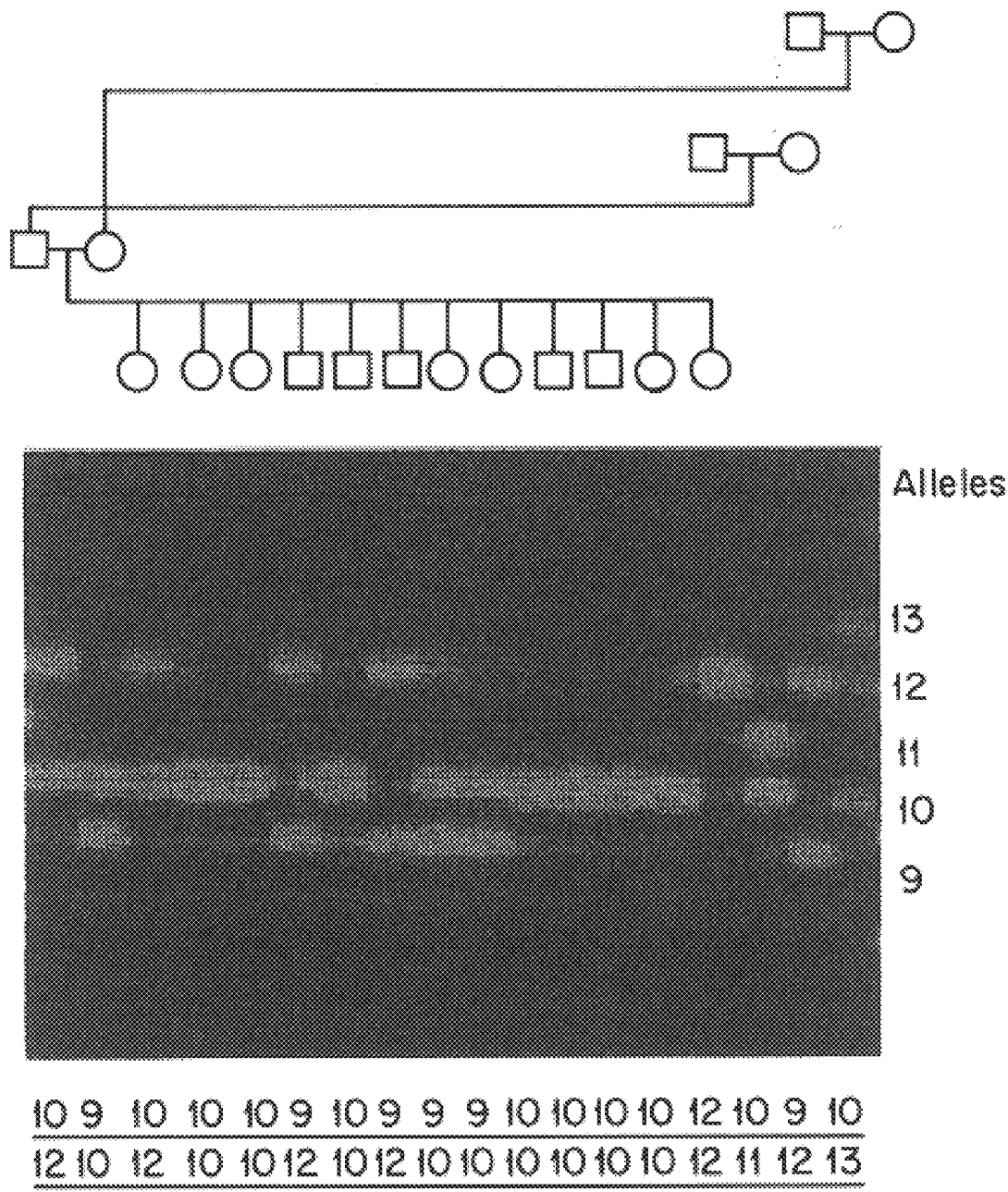
FIG. 3 is a family tree and electrophoretic gel showing different Xu-1 alleles from different family members.
Figure 4A:
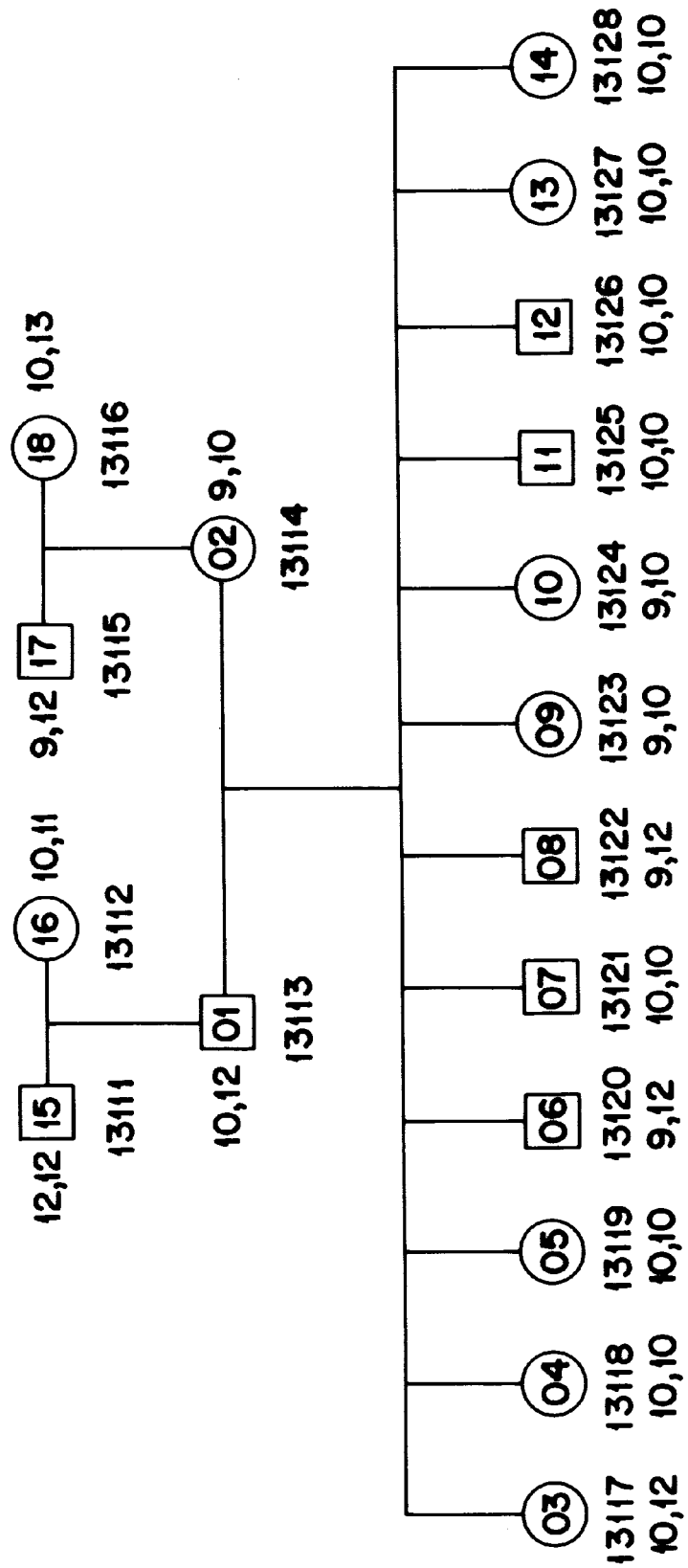
FIGS. 4A–4D shows various family trees, with Xu-1 allele data.
Figure 4B:
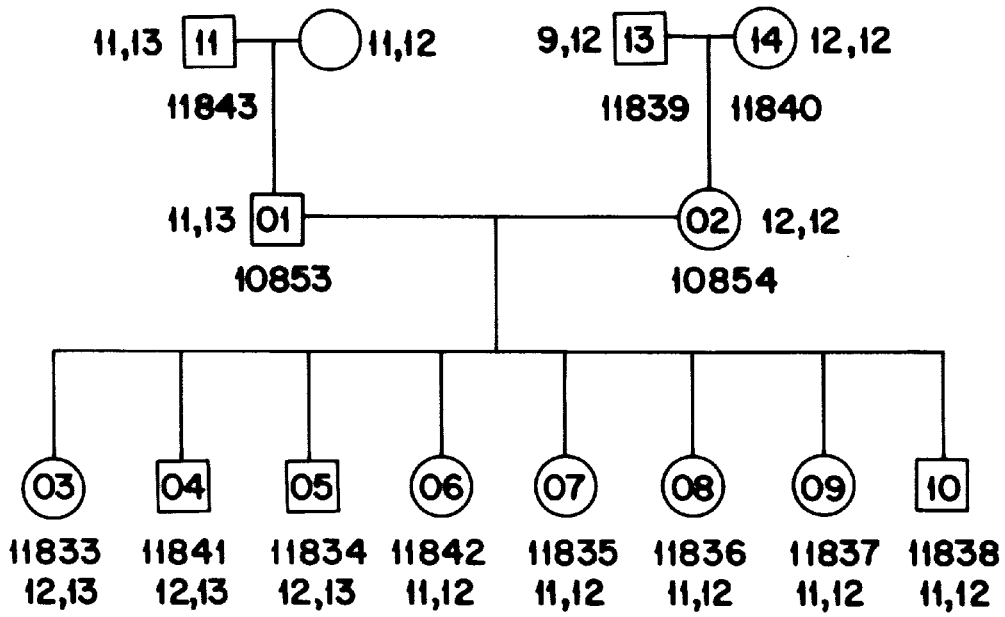
Figure 4C:
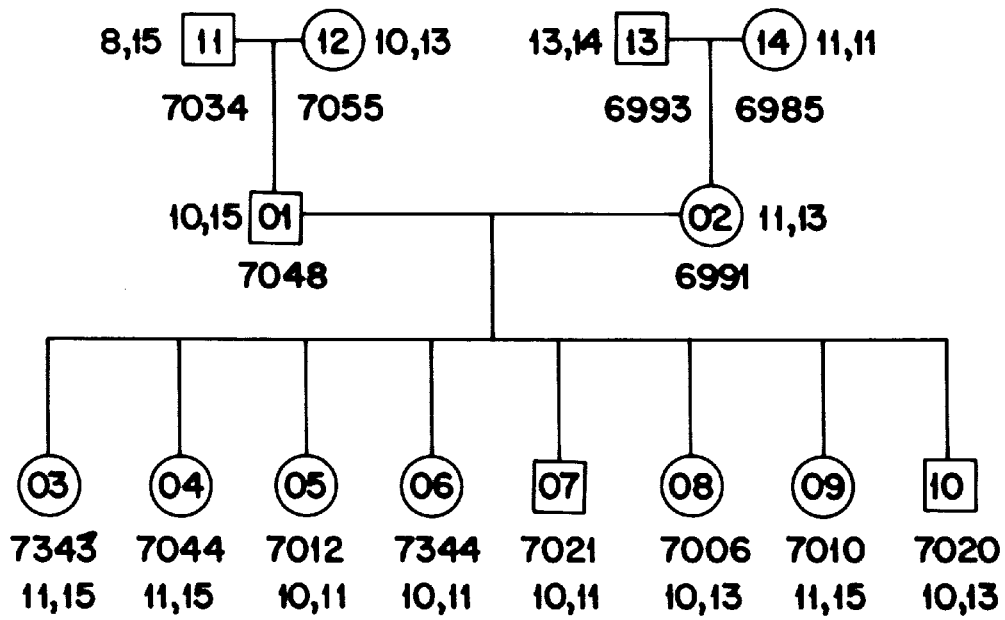
Figure 4D:
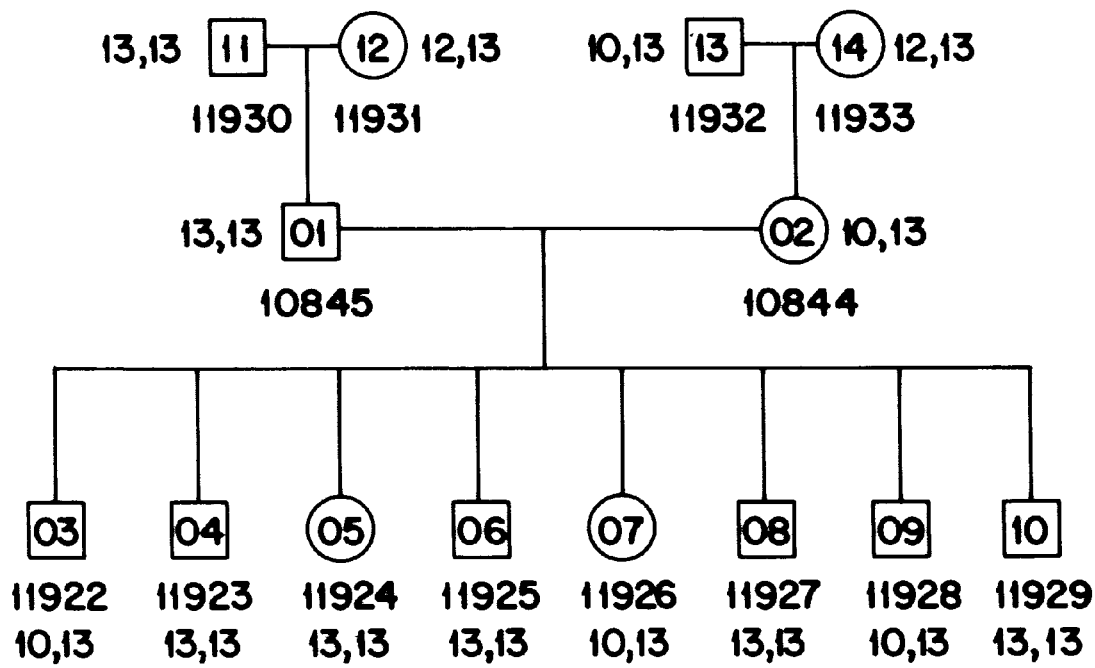

Data was obtained in a similar manner from 3 generations of a Caucasian (CEPH (Centre Etude Polymorpisme Humain)/Amish) family (pedigree 884). The results are shown in FIG. 3 in the form of a family tree and gel data showing Xu-1 allele data. The results are fully consistent and show Mendelian co-dominant inheritance. Other family groups have been similarly analysed and all show the same Mendelian co-dominant inheritance manner of this locus. for example, FIG. 4 shows the genotypes of four large CEPH families (pedigrees 884, 1424, 1341 and 1349).

EXAMPLE 5

By using a probe for the Xu-1 repeat in conjunction with a probe for another genetic marker, more detailed specific genetic information can be obtained about an individual, that is, a more detailed "genetic fingerprint" can be obtained, resulting in increased heterotygosity and hence usefulness of the results. Experiments were carried out using probes for the Xu-1 repat as described above, in conjunction with probes for a known trinucleotide repeat (ATT/TAA) present in the neuronal nitric oxide synthase (NOS1) gene in repeat numbers ranging from 5 to 13. The NOS1 repeat is described by Chung, E., Curus D., Chen, G., Marsdea, P. A., Twells. R., Xu, W. and Gardener, M. (1996) in Genetic evidence for the neuromal nitric oxide synthase gene as a susceptibility for infantile pyloric stenosis, Am. J. Hum. Genet. 58, 363–370.

For this purpose, PCR primers were designed for use with the NOS1 marker to give products in the range 110 to 138 bp, fluorescently labelled green with 5-Hexdye. The forward primer is 5'-GAAATTGGTCATAGTGGGAATG-3' (Seq. ID No. 3). The reverse primer is 5'-GTGTTGGTGAACCAACCCTCCTAA-3' (Seq. ID No. 4). This pair of the primers can be used under exactly the same PCR conditions as the primers for the Xu-1 repeat labelled with Famdye, so two PCR reactions can be performed at the same time.

Figure 5:
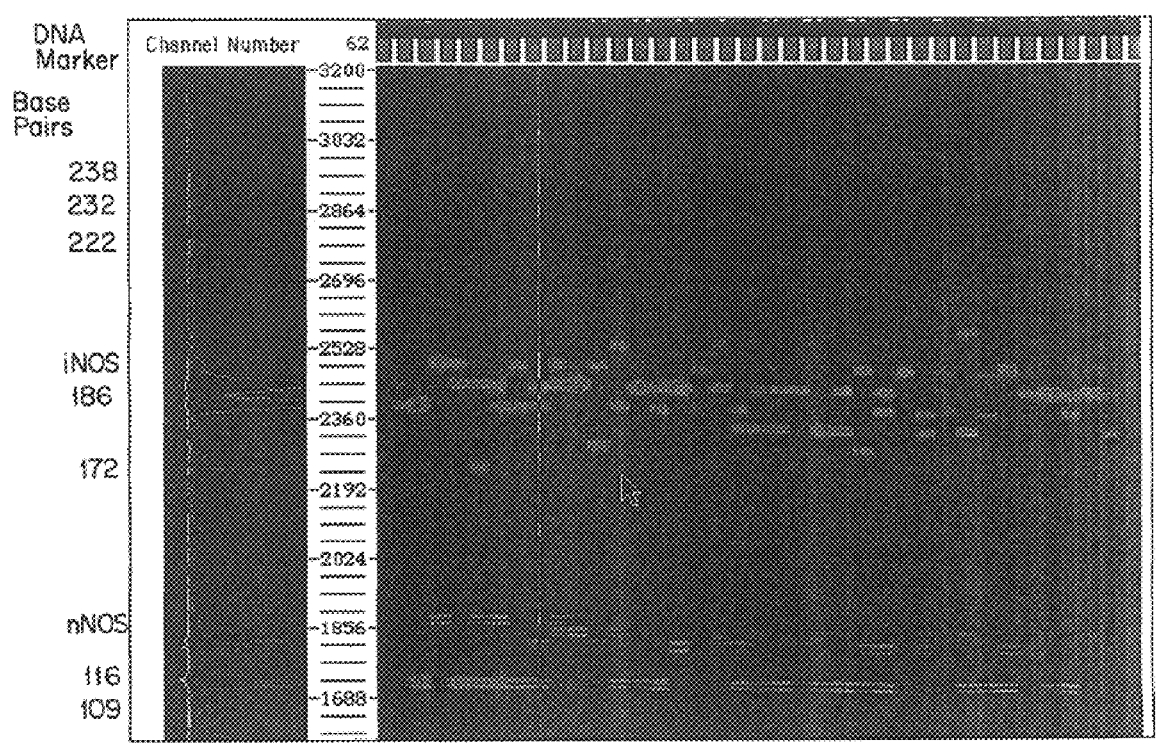
FIG. 5 shows an electrophoretic gel showing different Xu-1 alleles in combination with another microsatellite marker for different individuals.

FIG. 5 shows a Genescan gel obtained by this procedure, with the upper (blue) bands showing the Xu-1 repeats and the lower (green) bands the NCS1 repeats with results aligned for each sample. The combined heterozygeosity is about 99%.

EXAMPLE 6

Because the Xu-1 repeat of the invention is located at the 5' end of the human iNOS gene, which has been implicated in certain diseases including Alzheimer's disease, experiments were carried out on 112 deceased demented patients diagnosed by autopsy as having Alzheimer's disease, both the senile dementia Lewy body (SDLT) variant of Alzheimer's disease (22 patients) and non-Lewy body type (AD) (90 patients). For comparison, results were also obtained from 101 normal Caucasian individuals. The DNA for all subjects was obtained from the Cambridge Brain bank and was approved by the local ethics committee. Experiments were performed generally as described in Example 2.

Figure 6:
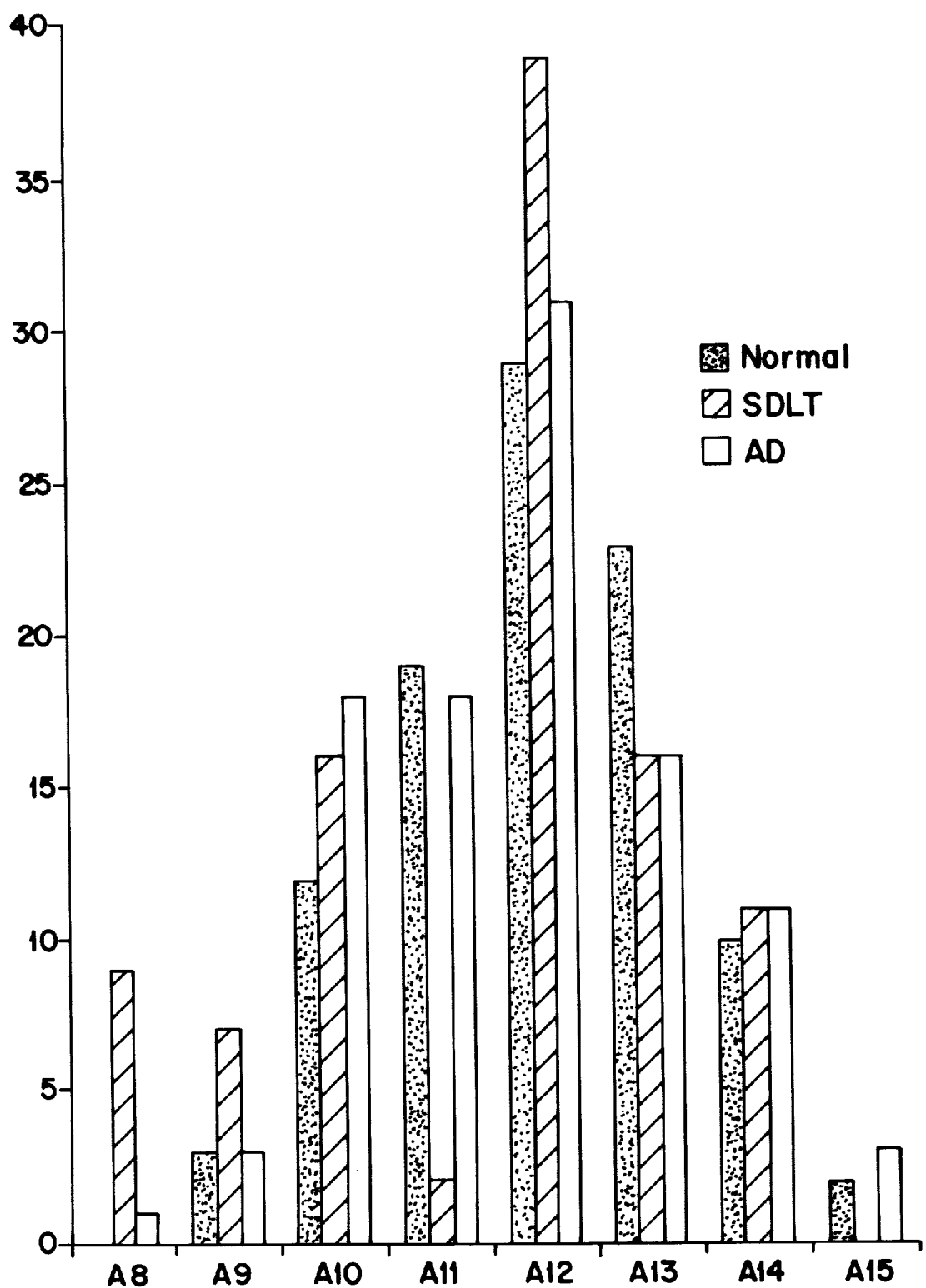
FIG. 6 is a chart showing the distribution of different Xu-1 alleles (A8 to A15) for a number of normal individuals, autopsied patients with the senile dementia Lewy body (SDLT) variant of Alzheimer's disease and non-Lewy body type Alzheimer's patents (AD) with the x axis showing % of chromosomes and the y axis showing the allele numbers.

The results are shown graphically in FIG. 6. The results show that most alleles have similar frequency in patients with Alzheimer's disease and non-demented controls. However, in samples from the SDLT patients, two smaller alleles, A8 and A9 (having 8 and 9 pentanucleotide repeats, respectively) are over-represented (16%, compared to normal 3% and AD 4%) and the A11 allele is under-represented (2% compared to normal 19%). Using the counting program from Linkage Utility, the p-value is calculated to be 0.0151 (6 degree freedom), which is much lower than required value 0.05 (5%). The results suggest that certain combinations of the Xu-1 pentanucleotide repeat variant in iNOS gene promoter, namely high A11 allele and/or low A8 and A9 alleles, may be associated with development of SDLT. This information may be of diagnostic or predictive value.

EXAMPLE 7

Figure 7:
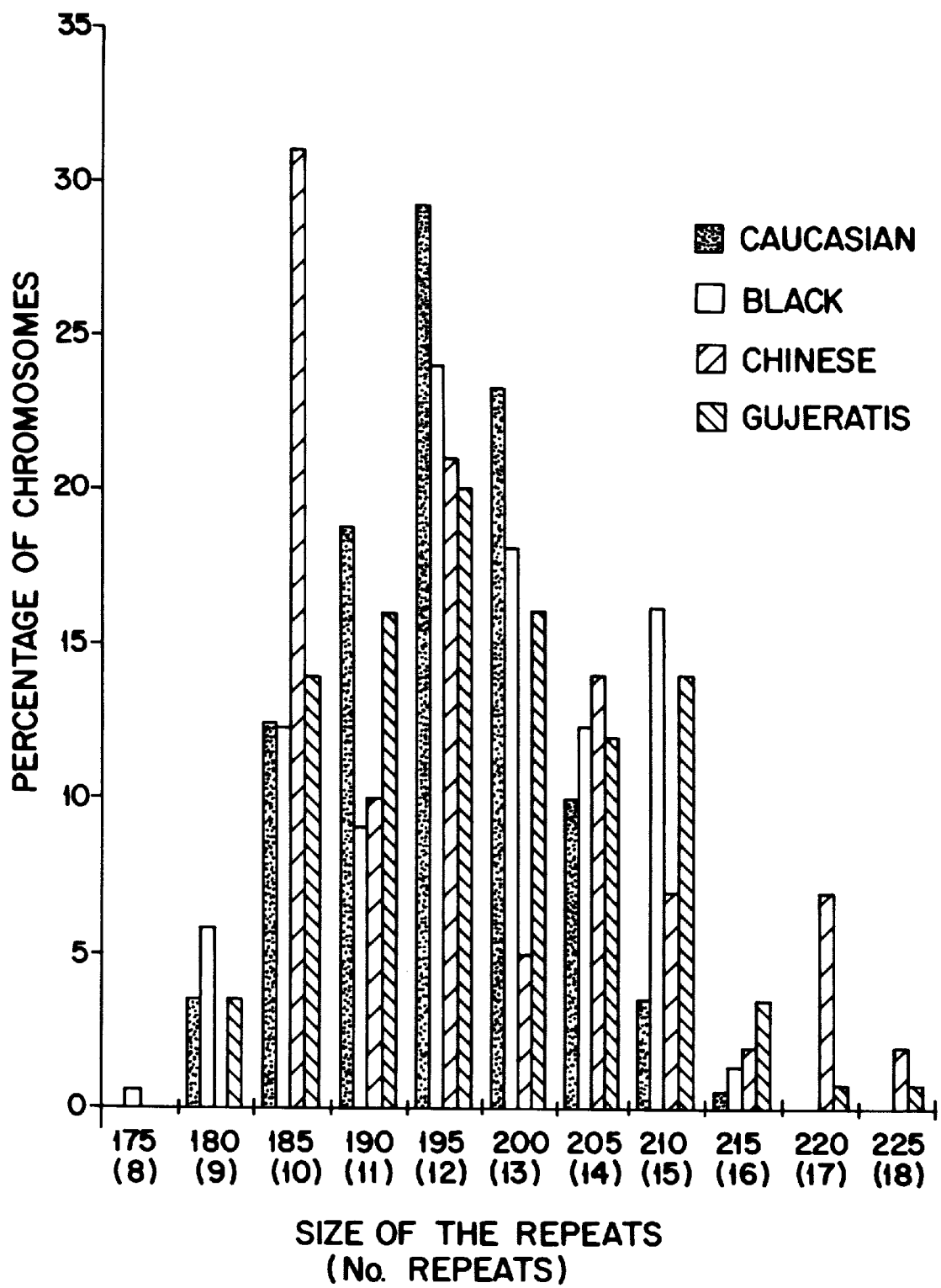
FIG. 7 is a chart similar to FIG. 6 showing the distribution of different Xu-1 alleles (A8 to A18) in Caucasian, Black, Chinese and Gujerati Asian populations.

Experiments were carried out in similar manner on 271 individuals (ie 542 chromosomes) of Caucasian, Black (Afro Caribbean and Afro American), Chinese and Gujerati Asian ethnic origin and the distribution of different numbers of the xu-1 repeat were analysed by ethnic group. The results are shown in tabular form in Tables 1 and 2, and graphically in FIG. 7. The degree of polymorphism is characterised by two indices: Heterozygosity (Heter) and polymorphism information content (PIC). For formulas and explanation, see Botstein, D., White, R. L. Skolnick, M. and Davis, R. W. Construction of a genetic linkage map in man using restriction fragment length polymorphisms. Am. J. Hum. Genet. 32:314–331. (1980). The overall heterozygosity was 0.841.

There are significant differences in allelic frequency of distribution apparent between the different ethnic groups. These results may therefore be of forensic value.

TABLE 1

| (CCTTT)n | Size (bp)* | Caucasian | Black | Chinese | Gujeratis | Combined |
|---|---|---|---|---|---|---|
| 8 | 175 | 0 | 1(0.006) | 0 | 0 | 1(0.002) |
| 9 | 180 | 7(0.035) | 9(0.058) | 0 | 5(0.035) | 21(0.039) |
| 10 | 185 | 25(0.124) | 19(0.123) | 13(0.31) | 20(0.139) | 77(0.142) |
| 11 | 190 | 38(0.188) | 14(0.09) | 4(0.10) | 23(0.16) | 79(0.146) |
| 12 | 195 | 59(0.292) | 37(0.24) | 9(0.21) | 29(0.20) | 134(0.247) |
| 13 | 200 | 47(0.233) | 28(0.181) | 2(0.05) | 23(0.16) | 100(0.184) |
| 14 | 205 | 20(0.10) | 19(0.123) | 6(0.14) | 17(0.22) | 62(0.114) |
| 15 | 210 | 5(0.035) | 25(0.162) | 3(0.07) | 20(0.14) | 53(0.098) |
| 16 | 215 | 2(0.005) | 2(0.013) | 1(0.02) | 5(0.035) | 9(0.017) |
| 17 | 220 | 0 | 0 | 3(0.07) | 1(0.007) | 4(0.007) |
| 18 | 225 | 0 | 0 | 1(0.02) | 1(0.007) | 2(0.004) |
| Total | | 202 | 154 | 42 | 144 | 542 |
| No. of alleles | | 8 | 9 | 9 | 10 | 11 |
| Heterozygosity | | 0.802 | 0.846 | 0.835 | 0.859 | 0.841 |
| PIC | | 0.769 | 0.82 | 0.793 | 0.835 | 0.81901 |

*Due to flanking sequences and running condition size varies +−2bp.

TABLE 2

| Population A: | Population B: | d.f. | $X^1$ | P value |
|---|---|---|---|---|
| Caucasian: | Black | 7 | 30.05 | 0.000083 |
| Caucasian: | Chinese | 7 | 34.89 | 0.000012 |
| Caucasian: | Gujeratis | 7 | 27 | 0.000235 |
| Black: | Chinese | 7 | 32.16 | 0.000038 |
| Black: | Gujeratis | 7 | 8.46 | 0.2938 |
| Chinese: | Gujeratis | 7 | 14.65 | 0.0407 |

What is claimed is:

1. A method of analyzing a genetic marker in an individual, said method comprising determining the number of contiguous repeats of sequence (CCTTT/GGAAA) in the inducible nitric oxide synthase (iNOS) gene in a biological sample obtained from said individual.

2. The method of claim 1 wherein said determining comprises the steps of contacting said sample with a pair of oligonucleotide primers, carrying out a polymerase chain reaction with said primers to amplify the contiguous repeats of sequence (CCTTT/GGAAA) in the iNOS gene and determining the number of contiguous repeats of sequence (CCTTT/GGAAA) in resulting products to determine the number of contiguous repeats of sequence (CCTTT/GGAAA) in the iNOS gene.

3. The method of claim 2 wherein the number of contiguous repeats in said products is determined by nucleotide sequencing.

4. The method according to claim 2 wherein said primer pair includes a forward primer having the sequence 5'-ACCCCTGGAAGCCTACAACTGCAT-3' (SEQ ID NO:1) and a reverse primer having the sequence 5'-GCCACTGCACCCTAGCCTGTCTCA-3' (SEQ ID NO:2).

5. The method according to one of claims 2–4, which further comprises contacting said sample with a second pair of oligonucleotide primers and determining the number of repeats of a second sequence.

6. The method according to claim 5, wherein said second sequence is the polymorphic trinucleotide repeat (ATT/TAA) of neuronal nitric oxide synthase (NOS1) gene.

7. The method according to claim 5 wherein said second pair of oligonucleotide primers includes a forward primer having the sequence 5'-GAAATTGGTCATAGTGGGAATG-3' (SEQ ID NO:3) and a reverse primer having the sequence 5'-GTGTTGGTGAACCAACCCTCCTAA-3' (SEQ ID NO:4).

8. The method of claim 2 wherein the number of contiguous repeats in said products is determined by gel electrophoresis.

9. A method of determining the number of contiguous repeats of sequence (CCTTT/GGAAA) in the inducible nitric oxide synthase (iNOS) gene of a sample of DNA, said method comprising contacting said sample with a pair of oligonucleotide primers, carrying out a polymerase chain reaction with said primers to amplify the contiguous repeats of sequence (CCTTT/GGAAA) in the iNOS gene and determining the number of contiguous repeats of sequence (CCTTT/GGAAA) in resulting products, thereby determining the number of contiguous repeats of sequence (CCTTT/GGAAA) in the iNOS gene.

10. The method of claim 9 wherein the number of contiguous repeats in said products is determined by nucleotide sequencing.

11. The method according to claim 9 wherein said primer pair includes a forward primer having the sequence 5'-ACCCCTGGAAGCCTACAACTGCAT-3' (SEQ ID NO:1) and a reverse primer having the sequence 5'-GCCACTGCACCCTAGCCTGTCTCA-3' (SEQ ID NO:2).

12. The method according to one of claims 9–11, which further comprises contacting said sample with a second pair of oligonucleotide primers and determining the number of repeats of a second sequence.

13. The method according to claim 12, wherein said second sequence is the polymorphic trinucleotide repeat (ATT/TAA) of neuronal nitric oxide synthase (NOS1) gene.

14. The method according to claim 12 wherein said second pair of oligonucleotide primers includes a forward primer having the sequence 5'-GAAATTGGTCATAGTGGGAATG-3' (SEQ ID NO:3) and a reverse primer having the sequence 5'-GTGTTGGTGAACCAACCCTCCTAA-3' (SEQ ID NO:4).

15. A primer pair comprising a forward primer having the sequence 5'-ACCCCTGGAAGCCTACAACTGCAT-3' (SEQ ID NO:1) and a reverse primer having the sequence 5'-GCCACTGCACCCTAGCCTGTCTCA-3' (SEQ ID NO:2), wherein said primer pair specifically amplifies contiguous repeats of sequence (CCTTT/GGAAA) in the inducible nitric oxide synthase (iNOS) gene.

16. a primer pair comprising a forward primer having the sequence 5'-GAAATTGGTCATAGTGGGAATG-3' (SEQ ID NO:3) and a reverse primer having the sequence 5'-GTGTTGGTGAACCAACCCTCCTAA-3' (SEQ ID NO:4), wherein said primer pair specifically amplifies a polymorphic trinucleotide repeat (ATT/TAA) of neuronal nitric oxide synthase (NOS1) gene.

17. The method of claim 9 wherein the number of contiguous repeats in said products is determined by gel electrophoresis.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (xi) SEQUENCE DESCRIPTION: SEQ ID NO: 1:

ACCCCTGGAA GCCTACAACT GCAT                                          24

(2) INFORMATION FOR SEQ ID NO: 2:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (xi) SEQUENCE DESCRIPTION: SEQ ID NO: 2:

GCCACTGCAC CCTAGCCTGT CTCA                                          24

(2) INFORMATION FOR SEQ ID NO: 3:

(i) SEQUENCE CHARACTERISTICS:
    (A) LENGTH: 22 base pairs
    (B) TYPE: nucleic acid -continued (C) STRANDEDNESS: single
        (D) TOPOLOGY: linear (xi) SEQUENCE DESCRIPTION: SEQ ID NO: 3:

GAAATTGGTC ATAGTGGGAA TG                                                  22

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 4:

GTGTTGGTGA ACCAACCCTC CTAA                                                24

(2) INFORMATION FOR SEQ ID NO: 5:

(i) SEQUENCE CHARACTERISTICS:
        (A) LENGTH: 383 base pairs
        (B) TYPE: nucleic acid
        (C) STRANDEDNESS: double
        (D) TOPOLOGY: linear (xi) SEQUENCE DESCRIPTION: SEQ ID NO: 5:

CTGCAGCAAG CCATAAACAT TCCCNTGGAG AAAGATGCTT TCCCAGCATC AAGATGAGAA    60

GATAACTTTT ATCAGCTCAG AGATGGCACC AGAGCCATCT ACAAATACCA AACAAACCTT   120

GCTATCCTAC TCCTTAGCTC ACTTCCACAT GTTTACCTTC TCACAGCTTG CCACCCCTGG   180

AAGCCTACAA CTGCATTCGT CTTGTCACCT TTCTCTTCTT TCTTTCTTTC TCTCTTTCCT   240

TTCCTTTCTT TTCCTTTCCT TTCCTTTCCT TTCCTTTCCT TTCCTTTCCT TTCCTTTCCT   300

TTCCTTTCCT CCTTTCCCTC TTTTTTTTCC TTTTTTTTTT GAGACAGGCT AGGGTGCAGT   360

GGCGCGACCA TAGCTCTCTG CAG                                          383